United States Patent [19]

Wang et al.

[11] Patent Number: 4,707,558

[45] Date of Patent: Nov. 17, 1987

[54] MONOMERS AND OLIGOMERS CONTAINING A PLURALITY OF VINYLBENZYL ETHER GROUPS, METHOD FOR THEIR PREPARATION AND CURED PRODUCTS THEREFROM

[75] Inventors: Chun S. Wang; Zeng-kun Liao, both of Lake Jackson; Dennis L. Steele, Freeport, all of Tex.

[73] Assignee: The Dow Chemical Company, Midland, Mich.

[21] Appl. No.: 903,165

[22] Filed: Sep. 3, 1986

[51] Int. Cl.$^4$ .............................................. C07C 149/12
[52] U.S. Cl. ........................................... 568/23; 568/33; 568/36; 568/37; 568/49; 568/333; 568/645; 568/646; 526/286; 526/333
[58] Field of Search ......................... 568/23, 33, 36, 37, 568/49, 333, 645, 646; 526/286, 333

[56] References Cited

U.S. PATENT DOCUMENTS

| | | | |
|---|---|---|---|
| 3,049,503 | 8/1962 | Milionis et al. | 568/333 |
| 4,116,936 | 9/1978 | Steiner | 526/268 |
| 4,170,711 | 10/1979 | Orlando et al. | 568/610 |
| 4,180,680 | 12/1979 | Dennis | 568/647 |
| 4,388,450 | 6/1983 | Crivello | 526/286 |
| 4,469,518 | 9/1984 | McKenzie | 106/90 |
| 4,482,381 | 11/1984 | Spitz et al. | 106/90 |
| 4,504,640 | 3/1985 | Harada et al. | 526/193 |
| 4,519,843 | 5/1985 | Willis et al. | 106/90 |
| 4,528,347 | 7/1985 | Harada et al. | 526/219 |
| 4,540,760 | 9/1985 | Harada et al. | 526/211 |
| 4,604,451 | 8/1986 | Harada et al. | 525/328.2 |
| 4,605,701 | 8/1986 | Harada et al. | 525/107 |
| 4,614,593 | 9/1986 | Roark | 210/708 |

OTHER PUBLICATIONS

Australian Journal of Chemistry, 1968, vol. 21, pp. 2703-2710.
J. Water Poll. Control Fed., 1966, vol. 38, pp. 1782-1804.
Translation of S. Harada, Kobunshi Kako, 1984, vol. 33, No. 10, pp. 21 et seq.
Translation of Japanese Brochure of Nitto Boseki Co., Ltd., entitled Polyallylamine Hydrochloride.

*Primary Examiner*—Paul R. Michl
*Assistant Examiner*—Alex H. Walker

[57] ABSTRACT

Monomers and oligomers containing a plurality of vinylbenzyl ether groups are prepared by reacting a material containing a plurality of aromatic hydroxyl groups such as tetramethyltetrabromobisphenol A with a vinylbenzyl halide such as vinylbenzyl chloride in the presence of a polar aprotic solvent such as dimethylformamide. The monomers and oligomers prepared by this process have an improvement in one or more properties selected from dielectric constant (before and/or after moisture absorption) or thermal stability. Also disclosed are new monomers and oligomers containing a plurality of vinylbenzyl ether groups such as bis(vinylbenzyl)ether of dicyclopentadienyl bisdimethylphenol.

18 Claims, No Drawings

MONOMERS AND OLIGOMERS CONTAINING A PLURALITY OF VINYLBENZYL ETHER GROUPS, METHOD FOR THEIR PREPARATION AND CURED PRODUCTS THEREFROM

BACKGROUND OF THE INVENTION

The present invention pertains to new compounds containing a plurality of vinylbenzyl groups and a method for their preparation.

Monomers having a plurality of vinylbenzyl ether groups have been prepared by Steiner in U.S. Pat. No. 4,116,936 and Orlando et al in U.S. Pat. No. 4,170,711 by a process which comprises reacting a material having a plurality of aromatic hydroxyl groups with a vinylbenzyl halide in the presence of an alkali metal hydroxide and a solvent such as an alcohol. The monomers and oligomers prepared by this process have only a portion of the aromatic hydroxyl groups present converted to vinylbenzyl ether groups. It has been discovered that when the solvent employed is a polar aprotic solvent that more than 95% of the aromatic hydroxyl groups present converted to vinylbenzyl ether groups which results in an improvement in one or more of the properties selected from dielectric constant (before and/or after moisture absorption) or thermal stability. Also, the monomers and oligomers prepared by the process of the present invention do not need further purification such as by recrystallization as described in U.S. Pat. No. 4,116,936.

SUMMARY OF THE INVENTION

One aspect of the present invention pertains to monomers or oligomers containing a plurality of vinylaryl ether groups represented by the following formulas I-III wherein A is a hydrocarbyl group having from 1 to about 25, preferably from 1 to about 15, most preferably from 1 to about 10, carbon atoms —O—, —S—, —S—S—,

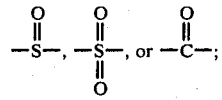

R is hydrogen or a hydrocarbyl group having from 1 to about 12, preferably from 1 to about 6, most preferably from 1 to about 4, carbon atoms, each X is independently hydrogen, a hydrocarbyl or hydrocarbyloxy group having from 1 to about 12, preferably from 1 to about 6, most preferably from 1 to about 4, carbon atoms or a halogen atom, preferably bromine; each m independently has a value of zero or 1; m' has a value of from zero to about 200, preferably from zero to about 50, most preferably from zero to about 20 and each n independently has a value of zero or one; with the proviso that when m' and n have a value of zero then A is a dicyclopentadienyl group or a dicyclopentadienyl oligomer group.

Another aspect of the present invention pertains to a method for the preparation of materials containing a plurality of vinylbenzyl ether groups which comprises reacting at least one alkali metal phenoxide of a material containing a plurality of aromatic hydroxyl groups with a vinylbenzyl halide in the presence of a polar aprotic solvent and subsequently recovering therefrom a material wherein more than about 95% of the aromatic hydroxyl groups have been converted to vinylbenzyl ether groups.

Another aspect of the present invention pertains to a method for the preparation of materials containing a plurality of vinylbenzyl ether groups which method comprises (A) reacting at least one alkali metal phenoxide of a material containing a plurality of aromatic hydroxyl groups with at least one chain extender material

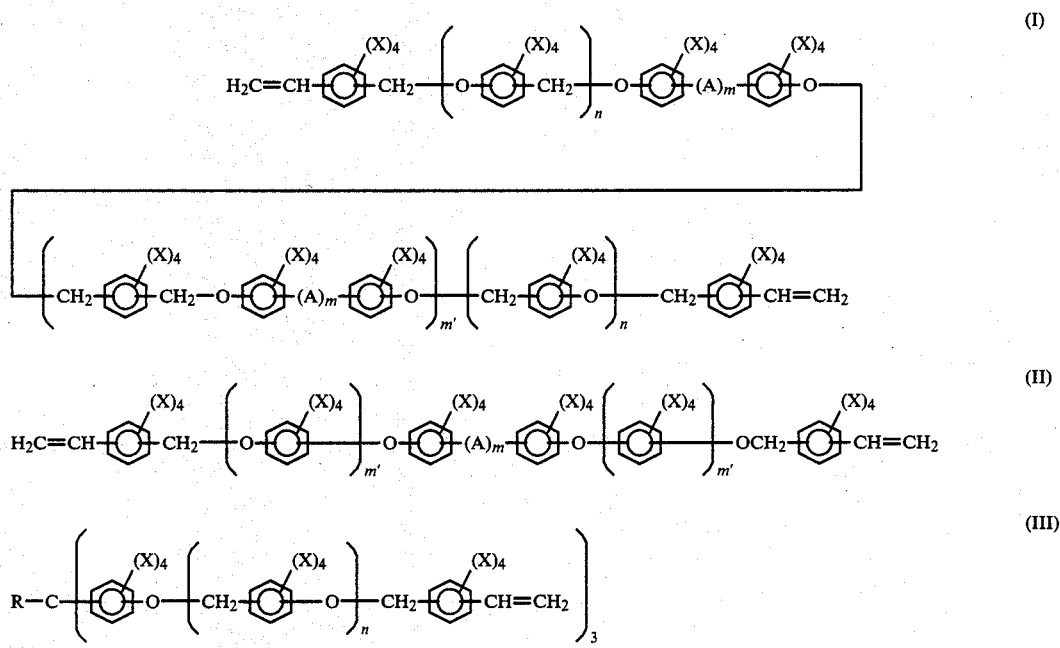

represented by the following formula IV

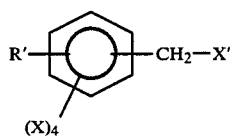

wherein R' is a hydroxyl group or a —CH₂X' group, X is as defined above and X' is a halogen, preferably chlorine or bromine in the presence of an alkali metal hydroxide and a polar aprotic solvent and then (B) reacting the alkali metal phenoxide of the resultant product with a vinylbenzyl halide in the presence of a polar aprotic solvent and subsequently recovering therefrom a material wherein more than about 95% of the aromatic hydroxyl groups have been converted to vinylbenzyl ether groups.

The term hydrocarbyl as employed herein includes, alkyl, cycloalkyl, cycloalkadienyl and oligomers thereof, aryl, aralkyl, alkaryl, alkenyl and the like. Likewise, the term hydrocarbyloxy as employed herein includes, alkyloxy, cycloalkyloxy, aryloxy, aralkyloxy, alkaryloxy, alkenyloxy and the like.

DETAILED DESCRIPTION OF THE INVENTION

The reaction between the aromatic hydroxyl-containing materials and the vinylbenzyl halide materials or when appropriate, the benzyl halide extender materials can be conducted at any suitable temperature which will substantially complete the reaction during the time employed. Suitable, temperatures include those from about −30° C. to about 100° C., preferably from about 0° C. to about 80° C., most preferably from about 15° C. to about 60° C. Suitable times include from about 0.5 to about 20, preferably from about 0.5 to about 15, most preferably from about 0.5 to about 6, hours.

Suitable hydroxyl-containing materials which can be employed herein include, for example, those represented by the following formulas V, VI and VII

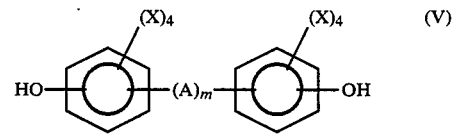

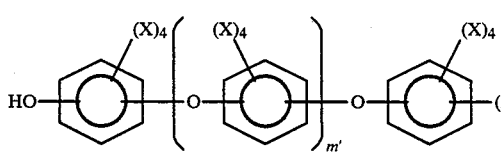
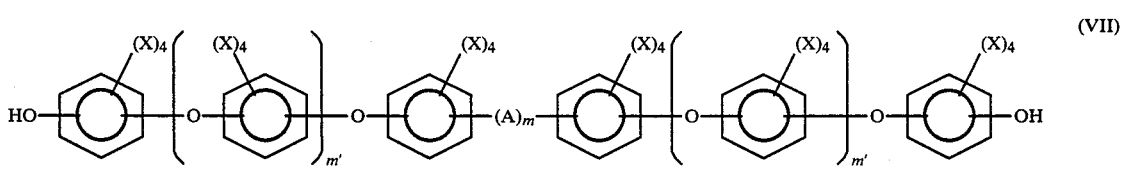

wherein A, R, X, m and m' are as defined above. Particularly suitable aromatic hydroxyl-containing materials include, for example, dicyclopentadienylbis(2,6-dimethyl phenol), dicyclopentadienyl bis(ortho-cresol), dicyclopentadienyl bisphenol, combinations thereof and the like. Such polycyclopentadienyl polyphenols and methods for their preparation can be found in U.S. Pat. No. 4,390,680 issued to Donald L., Nelson which is incorporated herein by reference. Also suitable hydroxyl-containing materials include, for example, resorcinol, bisphenol A, bisphenol F, bisphenol K, bisphenol sulfide, bisphenol sulfone, 3,3′,5,5′-tetramethyl bisphenol A, 3,3′,5,5′-tetramethyl bisphenol F, 3,3′,5,5′-tetramethyl bisphenol K, 3,3′,5,5′-tetramethyl bisphenol sulfide, 3,3′,5,5′-tetramethyl bisphenol sulfone, 3,3′,5,5′-tetramethyl biphenol 2,6-dibromo-3,3,′,5,5′-tetramethyl bisphenol F, 3,3′,5,5′-tetramethyl-2,2′,6,6′-tetrabromo biphenol, 1,1,1-tri-(hydroxyphenyl)alkanes, combinations thereof and the like. Suitable trihydroxyphenyl alkanes and method for their preparation can be found in U.S. Pat. No. 4,394,496 issued to Paul G. Schrader which is incorporated herein by reference.

Suitable vinylbenzyl halides which can be employed herein include, for example, vinylbenzyl chloride, vinylbenzyl bromide, combinations thereof and the like.

Particularly suitable benzyl halide chain extenders which can be employed herein include, for example, 4-bromomethyl-3,5-dibromo-2,6-dimethyl phenol, 2,4-bis(chloromethyl)mesitylene, 4,6-bis(chloromethyl)-m-xylene, 2,5-bis(chloromethyl)-p-xylene, 1,2-bis(bromomethyl)benzene, 1,3-bis(bromomethyl)benzene, 1,4-bis(bromomethyl)benzene, 1,2-bis(chloromethyl)benzene, 1,3-bis(chloromethyl)benzene, 1,4-bis(chloromethyl)benzene, combinations thereof and the like.

Suitable alkali metal hydroxides which can be employed herein include, for example, sodium hydroxide, potassium hydroxide, lithium hydroxide, combinations thereof and the like.

Suitable polar aprotic solvents which can be employed herein include, for example, glycol ethers, ketones, cyclic ethers, nitriles, sulfones, phosphoramides, combinations thereof and the like. Particularly suitable polar aprotic solvents include, for example, dimethylformamide, dimethylsulfoxide, dimethyl acetamide, N-methyl pyrrolidinone, dioxane, acetonitrile, tetrahydrofuran, ethylene glycol dimethyl ethers, 1,3-dimethoxy propane, 1,2-dimethoxy propane, tetramethylene sulfone, hexamethyl phosphoramide, methyl ethyl ketone, methyl isobutyl ketone, acetone, combinations thereof and the like.

The vinyl-containing materials of the present invention are useful as coating materials, molding resins, particularly electrical molding resins, adhesives and in preparing laminates similar to those made from unsaturated polyesters. The materials are also useful in preparing electrical laminates and the like.

The resins disclosed herein can be combined with a variety of monomers containing unsaturated substituents such as, for example, styrene, α-methyl styrene, divinyl benzene, vinyl toluene, acrylate and methacrylate esters and the like.

The vinyl benzyl ethers of polyphenols can also be blended with bismaleic anhydride imide, polycyanates, epoxy resins, liquid poly-1,2 or 1,4-butadiene, liquid epoxidized poly 1,2-butadiene, liquid butadiene-acrylonitrile copolymers, combinations thereof and the like.

The vinyl benzyl ethers of polyphenols can also be blended with additive or modifier materials such as, for example, fillers, pigments, dyes, stabilizers, plasticizers, flexibilizers, surfactants, reinforcing materials, fire retardants, diluents, combinations thereof and the like in conventional amounts.

The following examples are illustrative of the present invention but are not to be construed as to limiting the scope thereof in any manner.

EXAMPLE 1

To 1000 ml of a dimethylformamide (DMF) solution containing 282 g (0.75 mole) of dicyclopentadienyl-bis-(2,6-dimethyl phenol) in a reaction vessel equipped with a temperature control and indicating means, a means for stirring, cooling condenser and addition funnel was added 90 g (2.25 mole) sodium hydroxide at room temperature (~25° C.). The mixture was stirred under a nitrogen atmosphere for 4 hours (14400 s) at 40°-45° C. The mixture turned dark green in color when the formation of the sodium phenoxides was completed. The solution was then cooled to about 25° C. and 275 g of vinylbenzyl chloride (1.8 mole of a 60/40 by weight mixture of the m-/-isomers) was slowly added at 25°-30° C. over a period of 90 minutes (5400 s). After completion of the addition, the mixture was maintained at a temperature of 35° C. for 4 hours (14400 s) after which the solution turned blue in color. After maintaining the temperature at 45° C. for 2 hours (7200 s), the reaction mixture was cooled to room temperature and dry ice was added to neutralize any excess base. The DMF was removed by means of a rotating evaporator at 70° C. to 80° C. and a 10 mm Hg vacuum. Then 1000 ml of a 25/75 percent by weight mixture of toluene/methyl ethyl ketone was added to the syrupy residue. The solution was washed with 120-200 ml of water several times until the pH of the material was 7. The organic layer was separated and concentrated under a 5 mm to 10 mm vacuum at a temperature of 60° C. to 80° C. The 390 g of product obtained corresponded to a yield of 90% based on the dicyclopentadienyl-bis-(2,6-dimethyl phenol) without need for further purification. Infrared spectrum showed no residual phenolic hydroxyl groups remaining and chemical and ultraviolet (u.v.) analyses indicated that >99.9% conversion of the phenolic hydroxyl groups was achieved. The structure was confirmed by nuclear magnetic resonance (NMR) analysis to be the bis(vinyl benzyl)ethers of the dicyclopentadienyl-bis-(2,6-dimethyl phenol).

Castings were made by heating the above prepared thermally reactive oligomers to 60° to 80° C. until completely melted, degassing at <80° C. under a <5 mm Hg vacuum to remove entrapped air and then pouring into a preheated (100° C.) mold. The filled molds were heated at 120° C. to 130° C. for 1 hour (3600 s), 170° C. to 185° C. for 2 hours (7200 s) and finally 210° C. to 220° C. for 2 hours (7200 s). The cured resin has a Tg of 210° C. (by TMA) and 240° C. (by DMA). The properties of the cured resin are given in Table I.

The samples were tested employing the following procedures.

THERMAL TESTS

Glass transition temperatures and other thermal data were determined by using a Dupont 943 Thermo Mechanical Analyzer and a Dupont 982 Dynamic Mechanical Analyzer with a Dupont 1090 Thermal Analyzer.

Thermogravimetric analysis was conducted on a Perkin-Elmer TGS-2 system. The samples (approximately 10 mg) were heated at 10° C./min. (0.167° C./s) in a steady nitrogen stream of 35 cc/min. The isothermal weight loss in air after 250 hours (900,000 s) at 250° C. which is reported is based upon the number obtained from a 1"×2"×⅛" (25.4 mm×50.8 mm×3.175 mm) coupon.

MOISTURE RESISTANCE

The weight gain due to moisture absorption was measured periodically at room temperature after immersing the clear castings into boiling water at 100° C. The weight gain is based upon the average number obtained from three 1"×2"×⅛" (25.4 mm×50.8 mm×3.175 mm) coupons. The water on the surfaces of the coupons was carefully wiped off prior to weighing.

DIELECTRIC CONSTANT

The dielectric constants were obtained from 3"×3"×⅛" (76.2 mm×76.2 mm×3.175 mm) coupons measured with a Gen Rad 1689 bridge and a LD-3 cell.

COMPARATIVE EXPERIMENT A

The solvent disclosed in U.S. Pat. No. 4,116,936 was employed to prepare the product produced in Example 1. Thus, 94 g (0.25 mole) of dicyclopentadienyl-bis-o-cresol and 91.6 g (0.6 mole) of vinylbenzyl chloride, a 60/40 by weight mixture of the m-/p-isomers, were dissolved in 150 ml of acetone. The solution was heated to reflux and a solution of 49 g (0.75 mole) of potassium hydroxide (86%) in 100 ml of methanol was added over a period of 30 minutes (1800 s). The mixture was refluxed for an additional hour (3600 s). An additional 150 ml of acetone was added and the solution filtered to remove the precipitated potassium chloride. After adding 0.05 g of hydroquinone, the solution was evaporated to dryness on a rotating evaporator at 70° C. under a 5 mm to 10 mm vacuum. The viscous residual oil was worked up as described in Example 1 above. The resultant product was 119 g (76% yield based on dicyclopentadienyl bis-o-cresol) of bis-(vinylbenzyl)-ether of dicyclopentadienyl-bis-o-cresol with only 94% of the phenolic hydroxyl groups converted as determined by chemical and u.v. analysis. Infrared spectrum showed the broad absorption band of residual phenolic hydroxyl groups appearing at 3400 to 3500 cm$^{-1}$. The product was cured as in example 1 and the results are given in Table I.

EXAMPLE 2

The same procedure of Example 1 was employed by reacting 270 g (0.78 mole) of dicyclopentadienyl-bis(ortho-cresol) in 1000 ml DMF with 93 g (2.33 mole) of sodium hydroxide at 40° C. for 4 hours (14400 s). The same color change was observed when 286 g (1.87 mole) of vinylbenzyl chloride was added at 30° C. After work-up as in example 1, 480 g of bis-vinylbenzyl ethers of dicyclopentadienyl-bis(o-cresol) was obtained which corresponded to a yield of 87% based on dicyclopentadienyl-bis(o-cresol) without further purification. Infrared (IR) spectrum showed no residual phenolic hydroxyl groups remaining and chemical and u.v. analyses indicated that ~99.9% conversion of the phenolic hydroxyl groups was achieved. The structure was confirmed by NMR analysis as the bis(vinyl benzyl)ethers of dicyclopentadienyl-bis(o-cresol). The product was cured as in Example 1 and the results are reported in Table I.

TABLE I

| Property | Example 1 | Comp. Expt. A | Example 2 |
|---|---|---|---|
| BEFORE CURING | | | |
| Gel Time @ 175° C., sec. | 360–420 | 300–360 | 300–360 |
| Exotherm | | | |
| Initial, °C. | 180 | 180 | 170 |
| Maximum, °C. | 220 | 220 | 220 |
| AFTER CURING | | | |
| Thermal Stability Temp. required to obtain 5% wt. loss, °C. | 415 | 355 | 395 |
| Wt. loss after aging at 250° C. for 250 hrs. (900,000 s) in air, % | 1.66 | N.D.[3] | 2.60 |
| Moisture pick-up after 200 hrs (720,000 s) in boiling water at 100° C., % | 0.3 | N.D.[3] | 0.5 |
| Dielectric Constant[1] Frequency, dry/wet[2] | | | |
| 1000 Hz | 2.713/2.860 | 2.863/3.009 | 2.820/N.D. |
| 2000 Hz | 2.711/2.854 | 2.861/3.007 | 2.816/N.D. |
| 5000 Hz | 2.709/2.851 | 2.859/3.004 | 2.812/N.D. |
| 10000 Hz | 2.705/2.849 | 2.857/3.001 | 2.807/N.D. |
| 20000 Hz | 2.697/2.837 | 2.855/2.999 | 2.797/N.D. |
| 50000 Hz | 2.699/2.838 | 2.851/2.994 | 2.798/N.D. |
| 100000 Hz | 2.686/2.827 | 2.848/2.988 | 2.784/N.D. |
| Dissipation Factor[1] Frequency, dry/wet[2] | | | |
| 1000 Hz | .00167/.00217 | .00149/.00170 | .00265/N.D. |
| 2000 Hz | .00167/.00212 | .00150/.00183 | .00259/N.D. |
| 5000 Hz | .00165/.00217 | .00161/.00205 | .00267/N.D. |
| 10000 Hz | .00176/.00240 | .00180/.00241 | .00273/N.D. |
| 20000 Hz | .00196/.00277 | .00206/.00302 | .00284/N.D. |
| 50000 Hz | .00248/.00370 | .00262/.00425 | .00310/N.D. |
| 100000 Hz | .00289/.00460 | .00313/.00552 | .00343/N.D. |

[1]Dielectric constant and dissipation factor were measured at room temperature.
[2]This property was determined after 200 hours (720,00 s) in 100° C. boiling water.
[3]This property was not determined.

COMPARATIVE EXPERIMENT B

The solvent disclosed in U.S. Pat. No. 4,116,936 was employed to prepare the product produced in Example 2. Thus, 65 g (0.187 mole) of dicyclopentadienyl-bis-o-cresol and 71 g (0.467 mole) of vinylbenzyl chloride, a 60/40 by weight mixture of the m-/p-isomers, were dissolved in 200 ml of acetone. The solution was heated to reflux and a solution of 36 g of potassium hydroxide (86%) in 115 ml of methanol was added over a period of 30 minutes (1800 s). The mixture was refluxed for an additional hour (3600 s). An additional 200 ml of acetone was added and the solution filtered to remove the precipitated potassium chloride. After adding 0.05 g of hydroquinone, the solution was evaporated to dryness on a rotating evaporator at 70° C. under a 5 mm to 10 mm Hg vacuum. The viscous residual oil was worked up as described in Example 1 above. The resultant product was 80 g (77% yield based on dicyclopentadienyl bis-o-cresol) of bis-vinylbenzyl ether of dicylopentadienyl bis-o-cresol with only 91% of the phenolic hydroxyl groups converted as determined by chemical and u.v. analysis.

EXAMPLE 3

A mixture containing 30 parts of divinyl benzene and 70 parts by weight of the divinyl benzyl ethers of dicyclopentadienyl bis(2,6-dimethyl phenol) prepared as in Example 1 was polymerized at 210° C. to 220° C. for 2 hours (7200 s). The product was a tough clear resin. This product is designated as Sample 1. The dielectric constant and dissipation factor are given in Table II.

The product of Example 2 was copolymerized with divinyl benzene by heating to 60° to 80° C. until completely melted, degassing at <80° under a <5 mm Hg vacuum to remove entrapped air and then pouring into a preheated (100° C.) mold. The filled molds were heated at 120° C. to 130° C. for 1 hour (3600 s), 170° C. to 185° C. for 2 hours (7200 s) and finally 210° C. to 220° C. for 2 hours (7200 s). This product is designated as Sample 2. The dielectric constant and dissipation factor are given in Table II.

TABLE II

| | Sample 1 | Sample 2 |
|---|---|---|
| Dielectric Constant Frequency, | | |
| 1000 Hz | 2.692 | 2.710 |
| 10000 Hz | 2.683 | 2.701 |
| 100000 Hz | 2.664 | 2.682 |
| Dissipation Factor Frequency, | | |
| 1000 Hz | 0.00192 | 0.00166 |
| 10000 Hz | 0.00188 | 0.00184 |
| 100000 Hz | 0.00241 | 0.00229 |

EXAMPLE 4

In a similar manner to Example 1, 51 g (0.2 mole) of methylene bis-(2,6-dimethyl phenol) was reacted with 64 g (0.42 mole) of vinyl benzyl chloride in the presence of 18 g (0.44 mole) of sodium hydroxide and 150 g of dimethylformamide. There was obtained 72 g of viscous product. The structure was confirmed by NMR and IR analysis as being the bis(vinyl benzyl)ethers of methylene bis(2,6-dimethyl phenol). The oligomer was cured at 120° C. to 130° C. for 1 hour (3600 s), 175° C. for 1 hour (3600 s), 200° C. for 2 hours (7200 s) and finally 230° C. for 3 hours (10,800 s). The properties of the product before and after curing are given in Table III.

TABLE III

| BEFORE CURING | |
|---|---|
| Gel Time @ 175° C., sec. | 540 |
| Exotherm | |
| Initial, °C. | 180 |
| Maximum, °C. | 220–230 |
| AFTER CURING | |
| Thermal Stability Temp. required to obtain 5% wt. loss, °C. | 375 |
| Wt. loss after aging at 250° C. for 250 hrs. (900,000 s) in air, % | 3.44 |
| Moisture pick-up after 100 hrs (360,000 s) in boiling water at 100° C., % | 0.4 |

EXAMPLE 5

The procedure of Example 1 was repeated except that 109 g (0.2 mole) of tetrabromobisphenol A was employed instead of the dicyclopentadienyl bis(2,6-dimethyl phenol). The 125 g of product had no residual phenolic hydroxyl groups as determined by IR analysis. The structure of bis(vinyl benzyl)ethers of tetrabromobisphenol A as described in U.S. Pat. No. 4,116,936 was confirmed by NMR analysis. The product had a gel time of 2–5 minutes (120–300 s) at 175° C. A clear casting cured as in Example 1 had the following properties. Temperature required to obtain a 5% wt. loss was 315° C. The weight loss after aging at 250° C. for 250 hours (900,00 s) in air was 38.29%.

We claim:

1. A monomer of oligomer containing a plurality of vinylaryl ether groups represented by the following formulas I, II or III

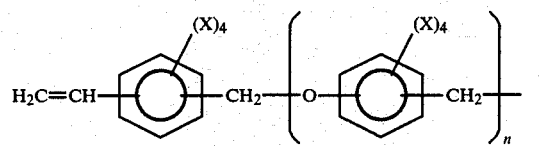

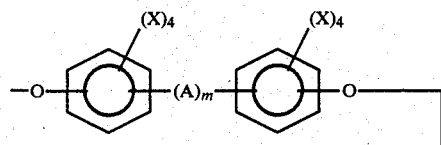

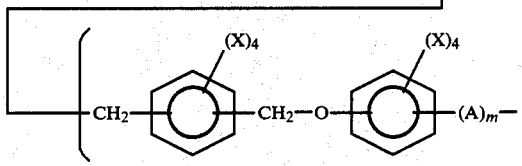
(I)

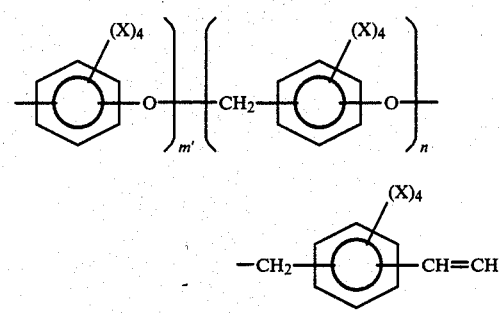
(II)

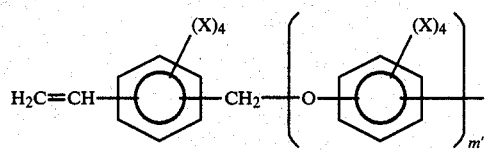

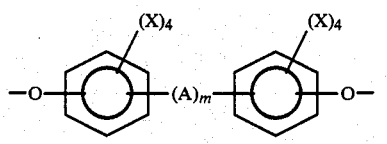

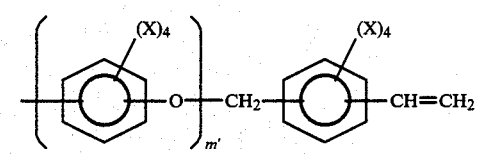
(III)

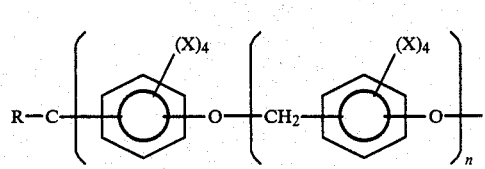

-continued

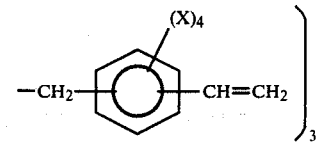

wherein A is a hydrocarbyl group having from 1 to about 25 carbon atoms, —O—, —S—, —S—S—,

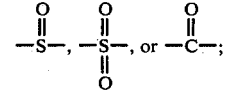

R is hydrogen or a hydrocarbyl group having from 1 to about 12 carbon atoms; each X is independently hydrogen, a hydrocarbyl or hydrocarbyloxy group having from 1 to about 12 carbon atoms or a halogen atom; m' has a value of from zero to about 200; each m and n independently has a value of zero or one; with the proviso that when m' and n have a value of zero, then A is a dicyclopentadienyl group or a dicyclopentadienyl oligomer group.

2. A monomer or oligomer of claim 1 wherein A is a hydrocarbyl group having from 1 to about 15 carbon atoms; R is hydrogen or a hydrocarbyl group having from 1 to about 6 carbon atoms; each X is independently hydrogen, a hydrocarbyl or hydrocarbyloxy group having from 1 to about 6 carbon atoms or a halogen atom; each m and n independently has a value of zero or 1; and m' has a value of from zero to about 50.

3. A monomer or oligomer of claim 1 wherein A is a hydrocarbyl group having from 1 to about 10 carbon atoms; R is hydrogen or a hydrocarbyl group having from 1 to about 4 carbon atoms; each X is independently hydrogen, a hydrocarbyl or hydrocarbyloxy group having from 1 to about 4 carbon atoms or a halogen atom; and m' has a value of from zero to about 20.

4. A monomer or oligomer selected from the group consisting of the bis(vinyl benzyl) ether of dicyclopentadienyl bis(2,6-dimethyl phenol), bis(vinyl benzyl) ether of dicyclopentadienyl bis(o-cresol), bis(vinylbenzyl)ether of 3,3,',5,5'-tetramethyl-2,2',6,6'-tetrabromobiphenol, and bis(vinylbenzyl)ether of 2,6-dibromo-3,3',5,5'-tetramethyl bisphenol F. and 5. A method for the preparation of materials containing a plurality of vinylbenzyl ether groups which comprises reacting at least one alkali metal phenoxide of a material containing a plurality of aromatic hydroxyl groups with a vinylbenzyl halide in the presence of a polar aprotic solvent and subsequently recovering therefrom a material wherein more than about 95% of the aromatic hydroxyl groups have been converted to vinylbenzyl ether groups.

6. A method of claim 5 wherein the reaction is conducted at a temperature of from about −30° C. to about 100° C. for from about 0.5 to about 20 hours.

7. A method of claim 5 wherein the reaction is conducted at a temperature of from about 0° C. to about 80° C. for from about 0.5 to about 15 hours.

8. A method of claim 5 wherein the reaction is conducted at a temperature of from about 15° C. to about 60° C. for from about 0.5 to about 6 hours.

9. A method of claim 6 wherein (a) said alkali metal phenoxide of a material containing a plurality of aromatic hydroxyl groups is an alkali metal phenoxide of a material represented by the following formulas V, VI or VII

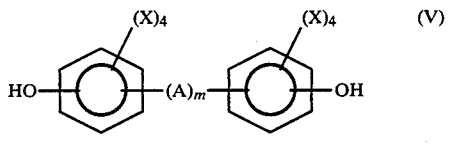 (V)

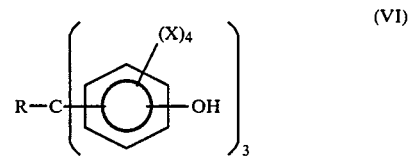 (VI)

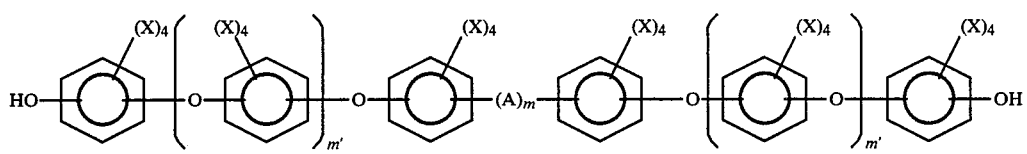 (VII)

wherein A is a hydrocarbyl group having from 1 to about 25 carbon atoms, —O—, —S—, —S—S—,

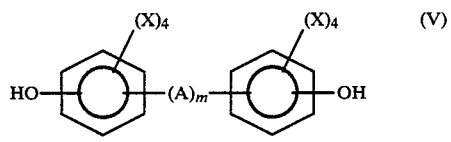 (V)

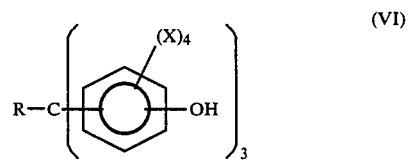 (VI)

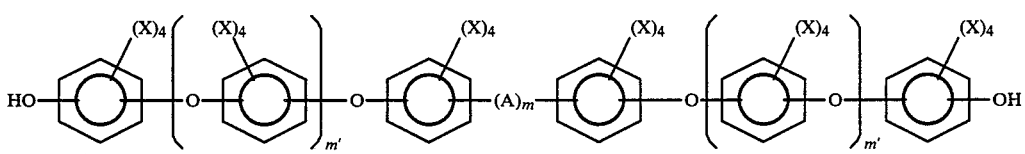 (VII)

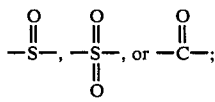

R is hydrogen or a hydrocarbyl group having from 1 to about 12 carbon atoms; each X is independently hydrogen, a hydrocarbyl or hydrocarbyloxy group having from 1 to about 12 carbon atoms or a halogen atom, preferably bromine; each m independently has a value of zero or 1; and m' has a value of from zero to about 200;

(b) said vinylbenzyl halide is vinylbenzyl chloride or vinylbenzyl bromide; and (c) said polar aprotic solvent is dimethylformamide, dimethylacetamide, dimethylsulfoxide, N-methyl pyrrolidinone, dioxane, acetonitrile, tetrahydrofuran, ethylene glycol dimethyl ether, 1,3-dimethoxy propane, 1,2-dimethoxy propane, tetramethylene sulfone, hexamethyl phosphoramide, methyl ethyl ketone, methyl isobutyl ketone, acetone or mixtures thereof.

10. A method of claim 7 wherein
(a) said alkali metal phenoxide of a material containing a plurality of aromatic hydroxyl groups is an alkali metal phenoxide of a material represented by the following formulas V, VI or VII

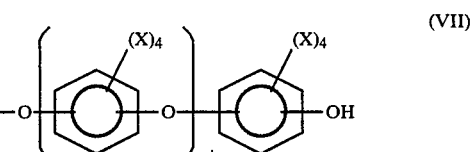 (VI)

(VII)

wherein A is a hydrocarbyl group having from 1 to about 15 carbon atoms; R is hydrogen or a hydrocarbyl group having from 1 to about 6 carbon atoms; each X is independently hydrogen, a hydrocarbyl or hydrocarbyloxy group having from 1 to about 6 carbon atoms or a halogen atom, preferably bromine; each m independently has a value of zero or 1; and m' has a value of from zero to about 50;

(b) said vinylbenzyl halide is vinylbenzyl halide is vinylbenzyl chloride or vinylbenzyl bromide; and (c) said polar aprotic solvent is dimethylformamide, dimethyl acetamide, dimethylsulfoxide, N-methyl pyrrolidinone, dioxane, acetonitrile, tetrahydrofuran, ethylene glycol dimethyl ether, 1,3-dimethoxy propane, 1,2-dimethoxy propane, tetramethylene sulfone, hexamethyl phosphoramide, methyl ether ketone, methyl isobutyl ketone, acetone or mixtures thereof.

11. A method of claim 8 wherein
(a) said alkali metal phenoxide of a material containing a plurality of aromatic hydroxyl groups is an alkali metal phenoxide of a material represented by the following formulas V, VI or VII

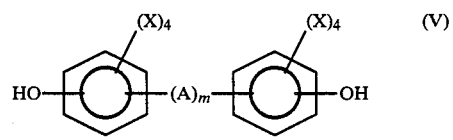 (V)

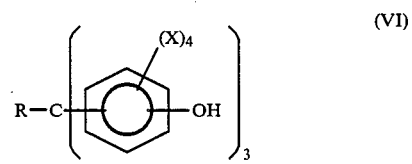 (VI)

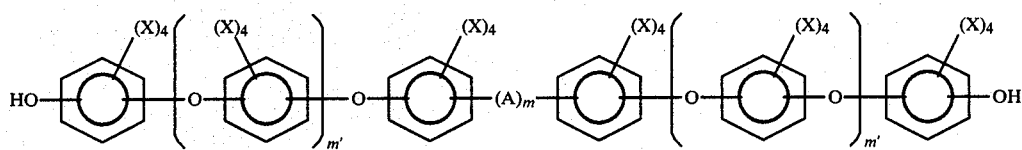

wherein A is a hydrocarbyl group having from 1 to about 10 carbon atoms; R is hydrogen or a hydrocarbyl group having from 1 to about 4 carbon atoms; each X is independently hydrogen, a hydrocarbyl or hydrocarbyloxy group having from 1 to about 4 carbon atoms or a halogen atom, preferably bromine; each m independently has a value of zero or 1; and m' has a value of from zero to about 20;

(b) said vinylbenzyl halide is vinylbenzyl chloride or vinyl benzyl bromide; and (c) said polar aprotic solvent is dimethylformamide, dimethylsulfoxide, N-methylpyrrolidinone, dioxane, acetonitrile, tetrahydrofuran, ethylene glycol dimethyl ether, 1,2-dimethoxy propane, tetramethylene sulfone, hexamethyl phosphoramide, methyl ethyl ketone, methyl isobutyl ketone, acetone or mixtures thereof.

12. A method for the preparation of materials containing a plurality of vinylbenzyl ether groups which comprises (A) reacting at least one alkali metal phenoxide of a material containing a plurality of aromatic hydroxyl groups with at least one chain extender material represented by the following formula IV

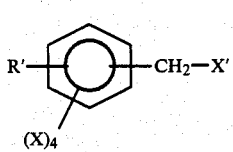

wherein R' is a hydroxyl group or a —CH₂X' group; each X is independently hydrogen, a hydrocarbyl or hydrocarbyloxy group having from 1 to about 12 carbon atoms or a halogen atom; and X' is a halogen; in the presence of a polar aprotic solvent and then (B) reacting the alkali metal phenoxide of the resultant product with a vinylbenzyl halide in the presence of a polar aprotic solvent and subsequently recovering therefrom a material wherein more than about 95% of the aromatic hydroxyl groups have been converted to vinylbenzyl ether groups.

13. A method of claim 12 wherein the reaction is conducted at a temperature of from about −30° C. to about 100° C. for from about 0.5 to about 20 hours.

14. A method of claim 13 wherein the reaction is conducted at a temperature of from about 0° C. to about 80° C. for from about 0.5 to about 15 hours.

15. A method of claim 14 wherein the reaction is conducted at a temperature of from about 15° C. to about 60° C. for from about 0.5 to about 6 hours.

16. A method of claim 13 wherein (a) said alkali metal phenoxide of a material containing a plurality of aromatic hydroxyl groups is an alkali metal phenoxide of a material represented by the following formulas V, VI or VII

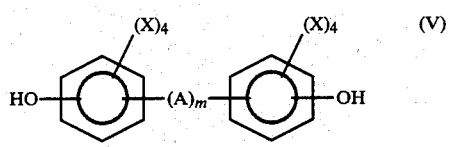

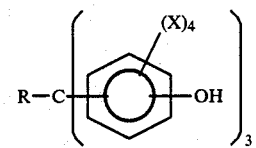

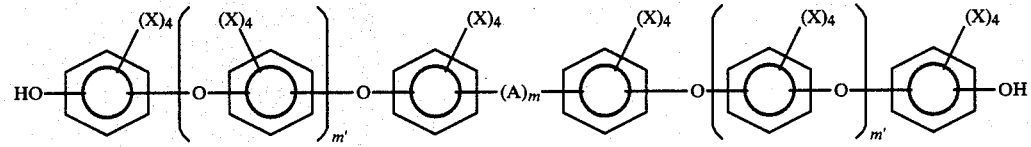

wherein A is a hydrocarbyl group having from 1 to about 25 carbon atoms, —O—, —S—, —S—S—,

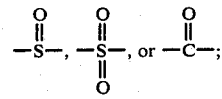

R is hydrogen or a hydrocarbyl group having from 1 to about 12 carbon atoms; each X is independently hydrogen, a hydrocarbyl or hydrocarbyloxy group having from 1 to about 12 carbon atoms or a halogen atom; each m independently has a value of zero or 1; and m' has a value of from zero to about 200;

(b) said extender material is 4-bromomethyl-3,5-dibromo-2,6-dimethyl phenol, 2,4-bis(chloromethyl)mesitylene, 1,2-bis(bromomethyl)benzene, 1,3-bis(bromomethyl)benzene, 1,4-bis(bromomethyl)benzene, 1,2-bis(chloromethyl)benzene, 1,3-bis(chloromethyl)benzene, 1,4-bis(chloromethyl)benzene, 4,6-bis-(chloromethyl)-m-xylene, 2,5-bis-(chloromethyl)-p-xylene, and combinations thereof;

(c) said vinylbenzyl halide is vinylbenzyl halide is vinylbenzyl chloride or vinylbenzyl bromide; and (d) said polar aprotic solvent is dimethylformamide, dimethylsulfoxide, N-methyl pyrrolidinone, dioxane, acetonitrile, tetrahydrofuran, ethylene glycol dimethyl ether, 1,2-dimethoxy propane, tetramethylene sulfone, hexamethyl phosphoramide, methyl ethyl ketone, methyl isobutyl ketone, acetone or mixtures thereof.

17. A method of claim 14 wherein
(a) said alkali metal phenoxide of a material containing a plurality of aromatic hydroxyl groups is an

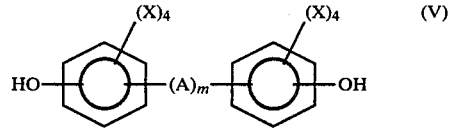   (V)

alkali metal phenoxide of a material represented by the following formulas V, VI or VII

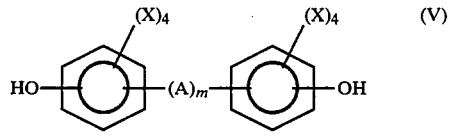   (V)

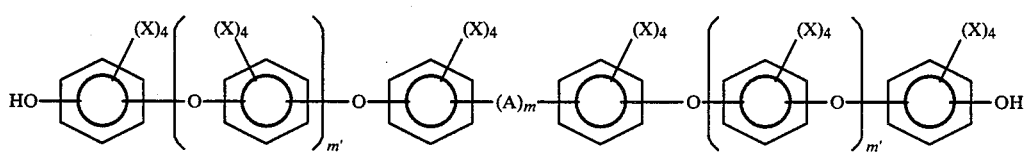

wherein A is a hydrocarbyl group having from 1 to about 15 carbon atoms, —O—, —S—, —S—S—,

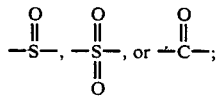

R is hydrogen or a hydrocarbyl group having from 1 to about 6 carbon atoms; each X is independently hydrogen, a hydrocarbyl or hydrocarbyloxy group having from 1 to about 6 carbon atoms or a halogen atom, preferably bromine; each m independently has a value of zero or 1; and m' has a value of from zero to about 50;

said extender material is 4-bromomethyl-3,5-dibromo-2,6-dimethyl phenol, 2,4-bis(-chloromethyl) 1,2-bis(bromomethyl)benzene, 1,3-bis(bromomethyl)benzene, 1,4-bis(bromomethyl)-benzene, 1,2-bis(chloromethyl)benzene, 1,3-bis(-chloromethyl)benzene, 1,4-bis(chloromethyl)benzene, 2,4-bis(chloromethyl)-mesitylene, 4,6-bis(-chloromethyl)-m-xylene, 2,5bis-(chloromethyl)-p-xylene, and combinations thereof;

(c) said vinylbenzyl halide is vinylbenzyl halide is vinylbenzyl chloride or vinylbenzyl bromide; and
(d) said polar aprotic solvent is dimethylformamide, dimethylsulfoxide, N-methyl pyrrolidinone, dioxane, acetonitrile, tetrahydrofuran, ethylene glycol dimethyl ether, 1,2-dimethoxy propane, tetramethylene sulfone, hexamethyl phosphoramide, methyl ethyl ketone, methyl isobutyl ketone, acetone or mixtures thereof.

18. A method of claim 15 wherein
(a) said alkali metal phenoxide of a material containing a plurality of aromatic hydroxyl groups is an alkali metal phenoxide of a material represented by the following formulas V, VI or VII

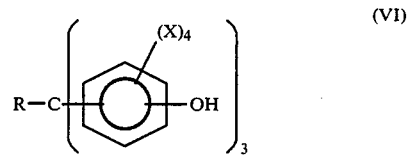   (VI)

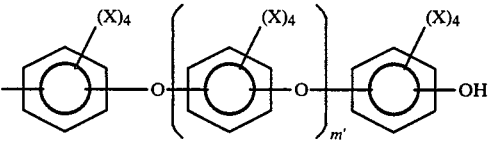   (VII)

wherein A is a hydrocarbyl group having from 1 to about 10 carbon atoms, —O—, —S—, —S—S—,

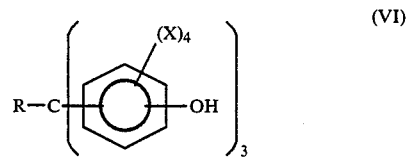   (VI)

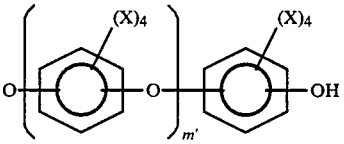   (VII)

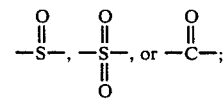

R is hydrogen or a hydrocarbyl group having from 1 to about 4 carbon atoms; each X is independently hydrogen, a hydrocarbyl or hydrocarbyloxy group having from 1 to about 4 carbon atoms or a halogen atom, preferably bromine; each m independently has a value of zero or 1; and m' has a value of from zero to about 20;

(b) said extender material is 4-bromomethyl-3,5-dibromo-2,6-dimethyl phenol, 2,4-bis(-chloromethyl) 1,2-bis(bromomethyl)benzene, 1,3-bis(bromomethyl)benzene, 1,4-bis(bromomethyl)-benzene, 1,2-bis(chloromethyl)benzene, 1,3-bis(-chloromethyl)benzene, 1,4-bis(chloromethyl)benzene, 2,4-bis-(chloromethyl)mesitylene, 4,6-bis-(chloromethyl)-m-xylene, 2,5-bis-(chloromethyl)-p-xylene, and combinations thereof;

(c) said vinylbenzyl halide is vinylbenzyl halide is vinylbenzyl chloride or vinylbenzyl bromide; and
(d) said polar aprotic solvent is dimethylformamide, dimethylsulfoxide, N-methyl pyrrolidinone, dioxane, acetonitrile, tetrahydrofuran, ethylene glycol dimethyl ether, 1,2-dimethoxy propane, tetramethylene sulfone, hexamethyl phosphoramide, methyl ethyl ketone, methyl isobutyl ketone, acetone or mixtures thereof.

* * * * *

UNITED STATES PATENT AND TRADEMARK OFFICE
CERTIFICATE OF CORRECTION

PATENT NO. : 4,707,558

DATED : November 17, 1987

INVENTOR(S) : Chun S. Wang, Zeng-kun Liao and Dennis L. Steele

It is certified that error appears in the above-identified patent and that said Letters Patent is hereby corrected as shown below:

1st page, under "References Cited", please delete all lines starting with U.S. 4,469,518 to the end of the last reference listed on the 2nd column.

Col. 1, line 67; insert a comma --,-- after "atoms".

Col. 2, line 9; delete the comma "," after "atoms" and insert therefore --;--.

Col. 3, line 33; delete the comma "," after "Suitable".

Col. 3, line 63; delete the comma "," after "L.".

Col. 4, line 3; change "biphenol" to --bisphenol-- and insert a comma --,-- after "bisphenol".

Col. 4, line 5; change "biphenol" to --bisphenol--.

Col. 5, line 27; change "m-/-isomers)" to --m-/p-isomers)--.

Col. 5, line 51; delete the 2nd occurrence of "the".

Col. 7, line 38; change "(720,00" to --(720,000--.

Col. 7, line 59; change "dicylopentadie-" to --dicyclopentadie- --.

Col. 8, line 6; change "<80°" to --<80°C--.

Col. 9, line 3; change "(900,00" to --(900,000--.

UNITED STATES PATENT AND TRADEMARK OFFICE
CERTIFICATE OF CORRECTION

PATENT NO. : 4,707,558

DATED : November 17, 1987

INVENTOR(S) : Chun S. Wang, Zeng-kun Liao and Dennis L. Steele

It is certified that error appears in the above-identified patent and that said Letters Patent is hereby corrected as shown below:

Col. 9, line 5; change 1st occurrence of "of" to --or--.

Col. 10, line 48; delete "and".

Col. 12, line 46; delete phrase "is vinylbenzyl halide".

Col. 12, line 53; change "ether" to --ethyl--.

Col. 12, line 58; change "pluraity" to --plurality--.

Col. 14, line 64; delete the phrase "is vinylbenzyl halide".

Col. 15, line 54; insert --(b)-- before "said".

Col. 15, line 61; change "2,5bis-(chloromethyl)-p-" to --2,5-bis-(chloromethyl)-p- --.

Col. 15, line 63; delete the phrase "is vinylbenzyl halide".

Col. 16, line 60; delete the phrase "is vinylbenzyl halide".

Signed and Sealed this

Fifteenth Day of November, 1988

Attest:

DONALD J. QUIGG

Attesting Officer

Commissioner of Patents and Trademarks